US012667422B2

(12) United States Patent
Riaz et al.

(10) Patent No.: US 12,667,422 B2
(45) Date of Patent: Jun. 30, 2026

(54) PERCUTANEOUS RETRIEVAL SYSTEM

(71) Applicant: Northwestern University, Evanston, IL (US)

(72) Inventors: Ahsun Riaz, Evanston, IL (US); Riad Salem, Evanston, IL (US); Abhinav Talwar, Evanston, IL (US)

(73) Assignee: Northwestern University, Evanston, IL (US)

( * ) Notice: Subject to any disclaimer, the term of this patent is extended or adjusted under 35 U.S.C. 154(b) by 314 days.

(21) Appl. No.: 18/485,835

(22) Filed: Oct. 12, 2023

(65) Prior Publication Data

US 2024/0180618 A1 Jun. 6, 2024

Related U.S. Application Data

(60) Provisional application No. 63/379,251, filed on Oct. 12, 2022.

(51) Int. Cl.
| | |
|---|---|
| *A61B 18/26* | (2006.01) |
| *A61B 17/00* | (2006.01) |
| *A61B 17/22* | (2006.01) |
| *A61B 17/225* | (2006.01) |
| *A61B 18/00* | (2006.01) |

(52) U.S. Cl.
CPC ............ *A61B 18/26* (2013.01); *A61B 17/225* (2013.01); *A61B 2017/00336* (2013.01); *A61B 2017/00539* (2013.01); *A61B 2017/22038* (2013.01); *A61B 2017/22067* (2013.01); *A61B* *2017/22079* (2013.01); *A61B 2018/00535* (2013.01); *A61B 2018/00982* (2013.01); *A61B 2217/007* (2013.01)

(58) Field of Classification Search
CPC .................. A61B 18/26; A61B 17/225; A61B 2017/00336; A61B 2017/00539; A61B 2017/22038; A61B 2017/22067; A61B 2017/22079; A61B 2018/00535; A61B 2018/00982; A61B 2217/007; A61B 17/22; A61B 17/221; A61B 2017/2215
See application file for complete search history.

(56) References Cited

U.S. PATENT DOCUMENTS

2020/0155293 A1* 5/2020 Morrison .............. A61F 2/0108

OTHER PUBLICATIONS

Andren-Sandberg et al., Complications and late outcome following percutaneous drainage of the gallbladder in acute calculous cholecystitis. Dig Surg. 2001;18(5):393-8.
Antalek et al., Gallbladder: Role of Interventional Radiology. Semin Intervent Radiol. Aug. 2021;38(3):330-339.
Ha et al., Cholecystectomy or not after percutaneous cholecystostomy for acute calculous cholecystitis in high-risk patients. Hepatogastroenterology. Sep.-Oct. 2008;55(86-87):1497-502.
Lee et al., Elective Laparoscopic Cholecystectomy is Better than Conservative Treatment in Elderly Patients with Acute Cholecystitis After Percutaneous Transhepatic Gallbladder Drainage. J Gastrointest Surg. Dec. 2021;25(12):3170-3177.
(Continued)

*Primary Examiner* — Ashley L Fishback
(74) *Attorney, Agent, or Firm* — David W. Staple; Casimir Jones, S.C.

(57) ABSTRACT

Provided herein are devices, systems, and methods for the percutaneous removal of solid deposits from the gallbladder or kidney.

16 Claims, 16 Drawing Sheets

(56) References Cited

OTHER PUBLICATIONS

Mckay et al., Short- and long-term outcomes following percutaneous cholecystostomy for acute cholecystitis in high-risk patients. Surg Endosc. May 2012;26(5):1343-51.

Mori et al., Tokyo Guidelines 2018: management strategies for gallbladder drainage in patients with acute cholecystitis (with videos). J Hepatobiliary Pancreat Sci. Jan. 2018;25(1):87-95.

Okamoto et al., Tokyo Guidelines 2018: flowchart for the management of acute cholecystitis. J Hepatobiliary Pancreat Sci. Jan. 2018;25(1):55-72.

Ozcan et al., Percutaneous Management of Biliary Stones. Semin Intervent Radiol. Aug. 2021;38(3):348-355.

Park et al., Long-term outcome and recurrence factors after percutaneous cholecystostomy as a definitive treatment for acute cholecystitis. J Gastroenterol Hepatol. Apr. 2019;34(4):784-790.

Peery et al., Burden of Gastrointestinal, Liver, and Pancreatic Diseases in the United States. Gastroenterology. Dec. 2015;149(7):1731-1741.e3.

Simorov et al., Emergent cholecystostomy is superior to open cholecystectomy in extremely ill patients with acalculous cholecystitis: a large multicenter outcome study. Am J Surg. Dec. 2013;206(6):935-40; discussion 940-1.

* cited by examiner

PERCUTANEOUS RETRIEVAL SYSTEM

CROSS-REFERENCE TO RELATED APPLICATION

The present invention claims the benefit of U.S. Provisional Patent Application Ser. No. 63/379,251, filed Oct. 12, 2022, which is hereby incorporated by reference in its entirety.

FIELD

Provided herein are devices, systems, and methods for the percutaneous removal of solid deposits from the gallbladder or kidney.

BACKGROUND

Acute calculous cholecystitis is a potentially serious inflammatory condition of the gallbladder that typically requires that a patient receive treatment in the hospital. Calculous cholecystitis, or blockage of the primary opening to the gallbladder (the cystic duct) by a gallstone, is the most common type of acute cholecystitis, accounting for approximately 90% of all cases.[2] Acute calculous cholecystitis occurs in the setting of cystic duct obstruction due to stones or sludge, resulting in a syndrome of right upper quadrant pain, fever, and leukocytosis.[3,4] Calculous cholecystitis is typically treated with laparoscopic cholecystectomy in patients who are medically fit to undergo surgery. In critically ill patients and patients who are non-surgical candidates (e.g., due to advanced age or co-morbidities), percutaneous cholecystectomy drains are routinely placed.[5,6]

Kidney stones (renal calculi, nephrolithiasis, or urolithiasis) are hard deposits made of minerals and salts that form inside your kidneys. Passing kidney stones can be quite painful, but the stones usually cause no permanent damage if they're recognized in a timely fashion. If stones become lodged in the urinary tract, are associated with a urinary infection or cause complications—surgery may be needed.

SUMMARY

Provided herein are devices, systems, and methods for the percutaneous removal of solid deposits from the gallbladder or kidney.

In some embodiments, provided herein are methods for the percutaneous removal of solid deposits from an internal organ of a subject, the methods comprising one or more of the steps of: (a) creating a percutaneous access tract into the internal organ; (b) inserting a guidewire via the percutaneous access tract, into the internal organ, and into an exit channel for the internal organ; (c) advancing an expandable occlusion element along the guidewire and positioning the expandable occlusion element within the exit channel; (d) expanding the expandable element to obstruct outflow from the internal organ through the exit channel; (e) inserting a sheath, into the internal organ via the percutaneous access tract; (f) performing lithotripsy to degrade the stones into smaller fragments; (g) advancing a separator through the sheath and into the internal organ; (h) applying a high-pressure flush from the end of the sheath and creating currents within the internal organ that carry the stones and/or fragments thereof into the sheath; and (i) retracting the separator into the distal end of the sheath, thereby trapping the stones and/or fragments thereof within the sheath. In some embodiments, methods, further comprising a step of (j) retracting the sheath through the percutaneous access tract, thereby removing the trapped stones and/or fragments thereof from the internal organ; or (j) retracting the separator through the sheath, thereby removing the trapped stones and/or fragments thereof from the internal organ. In some embodiments, methods comprise repeating one or more of the steps (e.g., steps (g)-(j)) one or more times (e.g., 1 time, 2 times, 3 times, 4 times, 5, times, 6 times, or more, or until all or substantially all (e.g., >90%, >95%, >99%) of the stones and/or stone fragments are removed from the internal organ).

In some embodiments, methods are provided for the percutaneous removal of solid deposits (e.g., stones) from the gallbladder of a subject. In some embodiments, the exit channel is a cystic duct and/or common bile duct.

In some embodiments, methods are provided for the percutaneous removal of solid deposits (e.g., stones) from the kidney of a subject. In some embodiments, the exit channel is the ureter.

In some embodiments, methods further comprise steps of advancing an expandable deformation element through the sheath; positioning it within the distal end of the sheath; and expanding the expandable deformation element to deform the distal end of the sheath into a funnel shape. In some embodiments, methods further comprise contracting the expandable element into a low-profile conformation and retracting the expandable element through the sheath, wherein the distal end of maintains the funnel shape upon contracting and retracting the second expandable element. In some embodiments, the expandable deformation element is a balloon or umbrella element.

In some embodiments, methods further comprise advancing an endoscope through the sheath and into the internal organ. In some embodiments, methods further comprise visualizing the internal organ and/or the stones or smaller fragments thereof with a camera near the distal end of the endoscope. In some embodiments, methods comprise advancing the separator through the endoscope and into internal organ.

In some embodiments, the separator is a balloon or umbrella element capable being advanced and retracted through the sheath and also capable of occluding the interior of the sheath to (i) prevent escape of the stones or fragments thereof from the sheath and (ii) to remove the stones or fragments thereof from the sheath as the separator is retracted through the sheath.

In some embodiments, creating a percutaneous access tract comprises creating incisions in the skin of the subject and the exterior surface of the internal organ.

In some embodiments, the expandable occlusion element is a balloon or umbrella element capable of adopting a collapsed conformation for being advanced along the guidewire and an expanded conformation for obstructing the exit channel of the internal organ.

In some embodiments, lithotripsy comprises extracorporeal shockwave lithotripsy, laser lithotripsy, or electrohydraulic lithotripsy.

In some embodiments, methods further comprise (k) collecting the stones or fragments thereof in a filter at the proximal end of the sheath. In some embodiments, the filter retains the stones or fragments thereof but allows liquid to pass through. In some embodiments, methods further comprise (l) collecting the liquid is a collection vessel.

In some embodiments, provided herein are systems, devices, components, and materials for performing the methods herein. In some embodiments, systems comprise (a) a guidewire; (b) an expandable occlusion element; (c) a sheath; (d) a lithotripsy generator; and (e) a separator element. In some embodiments, systems further comprise one or more of a second expandable element, an endoscope, a filter, and a collection vessel.

In some embodiments, provided herein are systems for the percutaneous removal of solid deposits from an internal organ within a subject, the system comprising: (a) a guidewire; (b) an expandable occlusion element capable of (1) being advanced along the guidewire, (2) being positioned at a desired position along the guidewire, and (3) adopting an expanded conformation at the desired positioned along the guidewire; (c) a sheath comprising: (1) a proximal end configured to be positioned outside of the subject, (2) a distal end configured to be positioned within the internal organ, and (3) an inner lumen extending from there proximal end to the distal end; (d) a lithotripsy generator; and (e) a separator element capable of (1) being advanced through the inner lumen of the sheath into the internal organ, (2) occluding the lumen of the sheath upon being retracted into the distal end of the sheath, and (3) withdrawing the contents of the inner lumen of the sheath from the subject upon being retracted through the inner lumen of the sheath.

In some embodiments, the sheath is reinforced to prevent compression or collapse under pressure exerted on the sheath by surrounding tissues, bones, etc. In some embodiments, the sheath is braided for reinforcement. In some embodiments, the sheath is capable of maintaining constant luminal diameter under the external pressure of the relevant anatomical environment.

In some embodiments, systems herein comprise a separator that is a balloon or umbrella element capable being advanced and retracted through the sheath and also capable of occluding the interior of the sheath to (i) prevent escape of the stones or fragments thereof from the sheath and (ii) to remove the stones or fragments thereof from the sheath as the separator is retracted through the sheath.

In some embodiments, systems herein comprise an expandable occlusion element that is a balloon or umbrella element capable of adopting a collapsed conformation for being advanced along the guidewire and an expanded conformation for obstructing the exit channel of the internal organ.

In some embodiments, systems herein comprise a lithotripsy generator capable of producing extracorporeal shockwave lithotripsy, laser lithotripsy, or electrohydraulic lithotripsy. In some embodiments, systems herein comprise one or more of a second expandable element, an endoscope, a filter, and a collection vessel. In some embodiments, the expandable deformation element is capable of being advanced through the sheath, positioned within the distal end of the sheath, and expanded to deform the distal end of the sheath into a funnel shape. In some embodiments, the expandable deformation element is a balloon or umbrella element. In some embodiments, the endoscope is capable of being advanced through the sheath into the internal organ. In some embodiments, the endoscope comprises a camera located at or near the distal end of the endoscope. In some embodiments, the endoscope comprises a channel through which the separator is advanced into the internal organ. In some embodiments, the endoscope comprises a channel through which a fluid can be flowed to flush the internal organ. In some embodiments, the collection vessel comprises a bag. In some embodiments, the collection vessel comprises a drain for releasing liquid from the collection vessel.

DETAILED DESCRIPTION

Provided herein are devices, systems, and methods for the percutaneous removal of solid deposits from the gallbladder or kidney.

In some embodiments, the systems, devices, components, and methods herein allow for stones to be removed from internal organs percutaneously. In some embodiments, a percutaneous access tract is created (e.g., via incision) for the direct purpose of the removal of stones. In other embodiments, a tract through the skin and into the organ for an alternative purpose (e.g., from a prior percutaneous cholecystectomy site) is used for the stone removal.

In some embodiments, systems herein include a device capable of occluding organ (e.g., kidney, gallbladder, etc.) outflow (e.g., with a compliant balloon); clear sheath that can be used to advance an endoscope and withdraw stones through; a device or component (e.g., balloon) capable of deforming the distal end of the sheath to create a funnel shape; a separator element (e.g., balloon, umbrella, etc.) that can be advanced through the endoscope and used to retain stones pulled into the sheath; a fluid flush generator and flush channel(s) capable of flushing the interior of the organ from the distal end of the endoscope; and external filer/collection component to collect stone and/or separate them from the fluids.

In some embodiments, exemplary methods are provided in FIGS. 3A-L and 4A-B for removing solid deposits (e.g., stones) from an internal organ (e.g., gallbladder of kidney) using exemplary systems, devices, and components herein.

Figure 1:
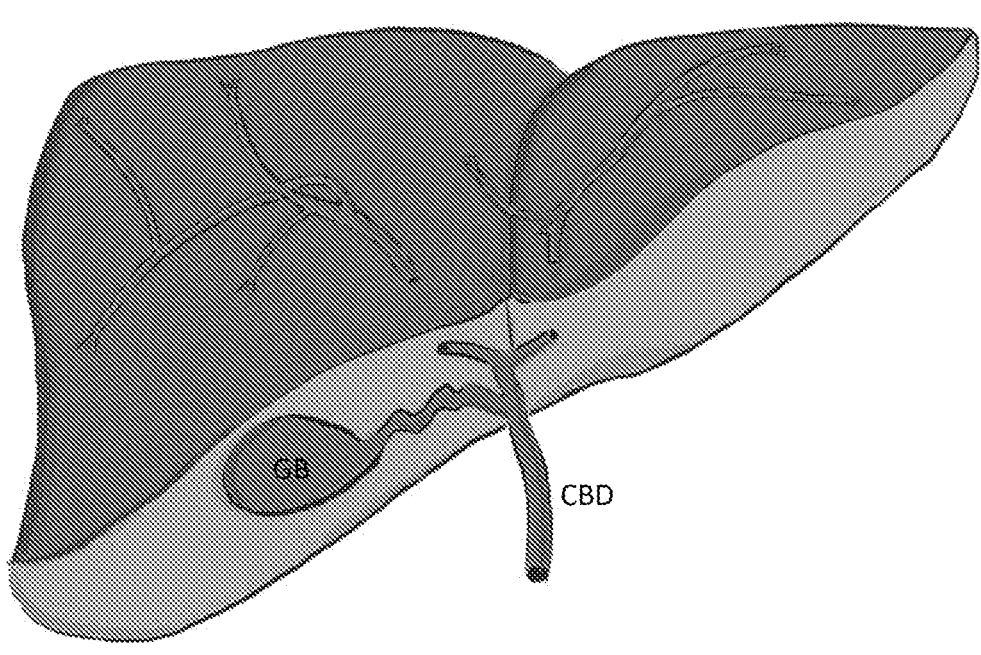
FIG. 1. Drawing depicting the anatomy of the gallbladder (GB) and the common bile duct (CBD).
Figure 2:
FIG. 2. Image of gallstones extracted using an exemplary technique and system.
Figure 3A:
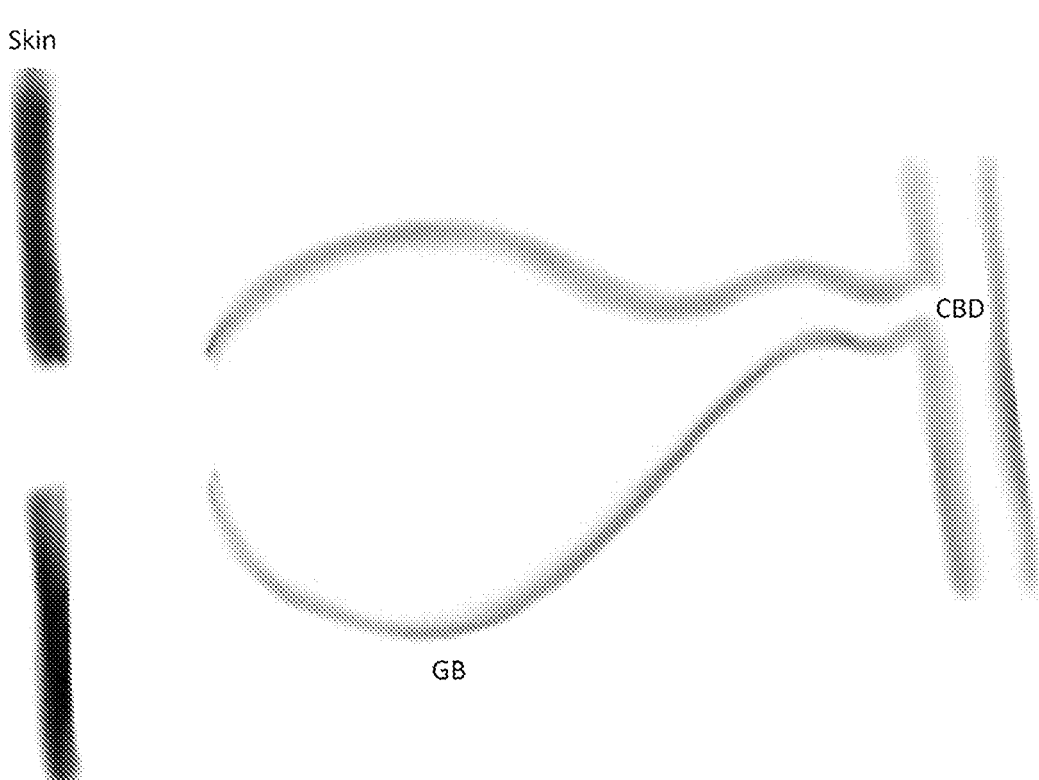
FIG. 3A-L. Drawings depicting an exemplary system and method for the removal of gallstones: (A) Exemplary percutaneous access tract through the skin and into the gallbladder; (B) Wire advanced from the exterior of the subject through the skin and into the gallbladder, extending through the cystic duct and common bile duct; (C) Exemplary compliant balloon advanced over the wire and inflated to obstruct gallbladder outflow at the cystic duct; (D) Sheath placed into the into the gallbladder via the percutaneous access tract; (E) A high-pressure balloon advanced through the sheath, aligned with the distal end of the sheath, and inflated to create a funnel shape at the end of the sheath; (F/G) Large gallstones are broken into smaller pieces using laser or electrohydraulic lithotripsy; (H) Endoscope advanced through the sheath into the gallbladder to visualize the stones (e.g., number, size, characteristic, etc.); (I) Compliant separator advanced through the working channel of the endoscope; (J) Scope is retracted into the sheath while keeping the separator remains outside the sheath in the gallbladder interior, thereby creating a space within the distal end of the sheath; (K) a high-pressure flush from the endoscope creates currents to push stones/stone fragments into the sheath; and (L) the separator is retracted into the sheath and stones/stone fragments are trapped within the sheath between the separator and the distal end of the endoscope. The scope and the separator are then retracted to remove the stones/fragments. Steps H to L are repeated as needed.

In some embodiments, methods comprise creating or accessing an existing percutaneous access tract through the skin and into an organ (e.g., kidney or gallbladder) (FIG. 3A). Existing knowledge of in the field allows for the skilled artisan to create a percutaneous access tract (e.g., surgically) and to access a percutaneous access tract with the systems, devices, and components described herein.

Figure 3B:
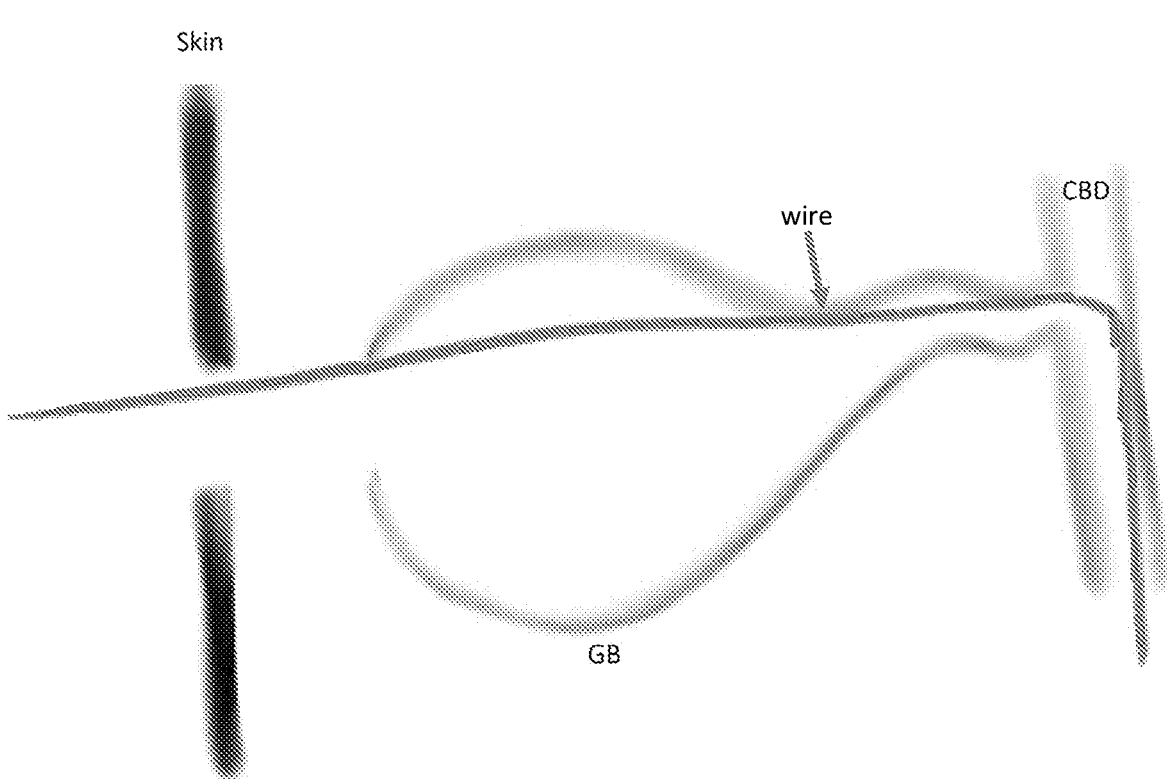

In some embodiments, a wire (e.g., guidewire) is inserted through the skin of the subject and into the internal organ to be treated via the percutaneous access tract (e.g., FIG. 3B). In particular embodiments, the guidewire is advanced from the exterior of the subject through the skin and into the gallbladder, extending through the cystic duct and common bile duct. In other embodiments, the guidewire is advanced from the exterior of the subject through the skin and into the kidney, extending into and/or through the ureter. In some embodiments, other internal organs may be accessed and treated for deposit removal via the methods described herein. Some embodiments herein require that outflow from the organ be obstructed in order to allow removal of deposits form the organ. In some embodiments, the natural outflow channel from the organ (e.g., cystic duct for the gallbladder, ureter for the kidney, etc.) is occluded using a component of a system herein. In some embodiments, an expandable occlusion element (e.g., balloon, umbrella, etc.) is advanced through the organ, into the outflow channel, and positioned at the occlusion site. Suitable expandable occlusion elements are capable of adopting a low-profile conformation that can be advanced and withdrawn through the percutaneous access tract (e.g., along a guidewire) and a higher-profile conformation capable of approximating the inner circumference of the occlusion site (e.g., within the ureter, cystic duct, etc.). Exemplary expandable occlusion elements include balloons (e.g., compliant balloons), umbrella elements, sail elements, etc.

Figure 3C:
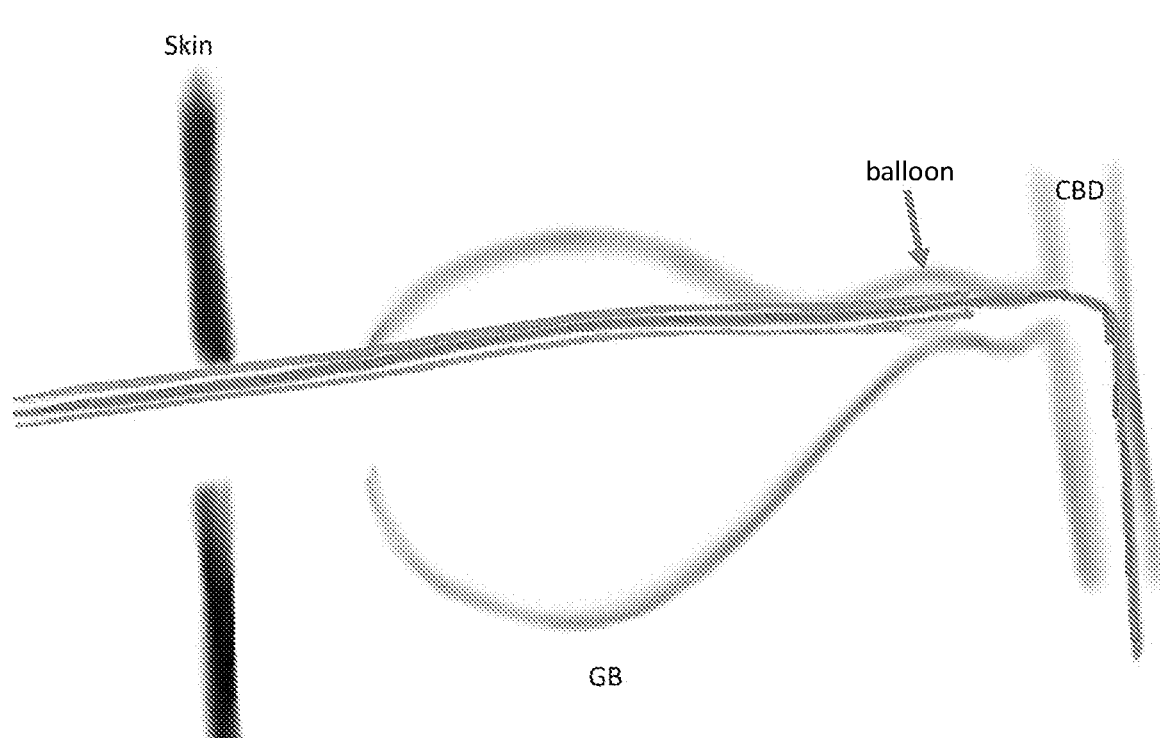

In some embodiments, the change in formation of the expandable occlusion element is triggered from outside the subject. For example, an occlusion balloon is inflated or filled with fluid (transferred via a lumen connected to the balloon) in order to transition from a low-profile conformation to the higher-profile conformation (e.g., in which the occlusion site is obstructed by the occlusion balloon) (FIG. 3C). In other embodiments, an expandable occlusion element at the occlusion site maintains a mechanical connection to the exterior of the subject (e.g., via the percutaneous access tract) that allows a user to expand/contract the element.

In some embodiments, the expandable occlusion element is compliant and capable of approximating irregular shapes of the inner wall of the occlusion site. In some embodiments, the expandable occlusion element is capable of obstructing at least 70% of the outflow via the exit channel of the organ when in the higher-profile conformation (e.g., 70%, 75%, 80%, 85%, 90%, 95%, 99%, or more or ranges therebetween).

Figure 3D:
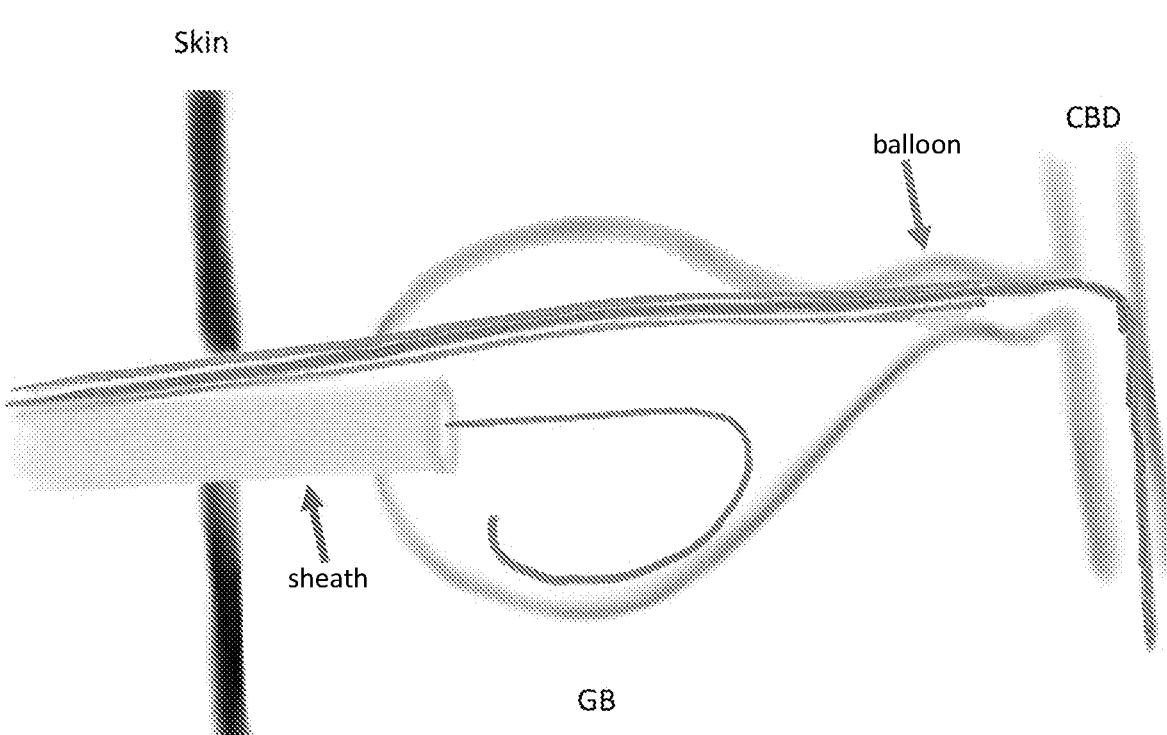

In some embodiments, a sheath is inserted via the percutaneous access tract and the distal end of the sheath is placed within the organ-to-be-treated (e.g., gallbladder, kidney, etc.) (FIG. 3D). In some embodiments, the sheath material is flexible. In some embodiments, the sheath material is transparent. Materials and dimensions for catheters and sheaths for medical access procedures are understood in the field. In some embodiments, the sheath provides easier access along the percutaneous access tract for various devices and components to be used in the methods herein. In some embodiments, one or more components and devices of the systems herein (e.g., endoscope, expandable deformation element, separator, etc.) are advanced through the sheath in order to access the treatment site.

Figure 3E:
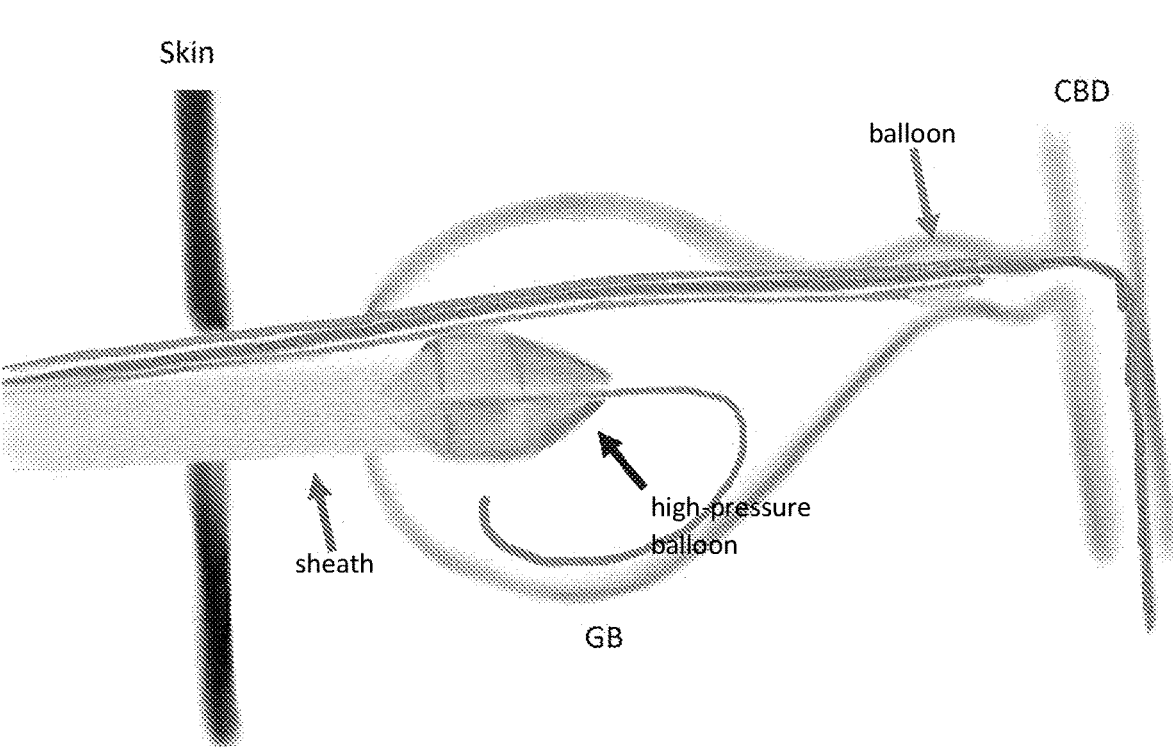

In some embodiments, the sheath provides a conduit through which the stones and fragments thereof are removed. In some embodiments, in order to facilitate the flow of stones/fragments into the sheath, the distal end of the sheath is deformed into an expanded mouth, when the distal end of the sheath is in place within the organ. In some embodiments, the sheath comprises an expansion element within the distal end of the sheath that allows the distal end to be deformed into a funnel like shape. Alternatively, an expandable deformation element may be deployed through the sheath and positioned within the distal end of the sheath. In some embodiments, the expandable deformation element is deployed in a low-profile, collapsed, or deflated conformation. When the expandable deformation element is expanded within the distal end of the sheath, the circumference of the portion of the sheath around the expandable deformation element is deformed (expanded). In some embodiments, the distal end of the sheath is deformed into a bowl or funnel shape, with the distal-most portion having a greater circumference that segments of the sheath that are less distal (FIG. 3E). In some embodiments, the expandable deformation element is a balloon or umbrella. In some embodiments, the expandable deformation element is a balloon capable of being filled to sufficiently high pressures, in order to deform the distal end of the sheath with the force exerted on the sheath by the expanding balloon within.

Figure 3F:
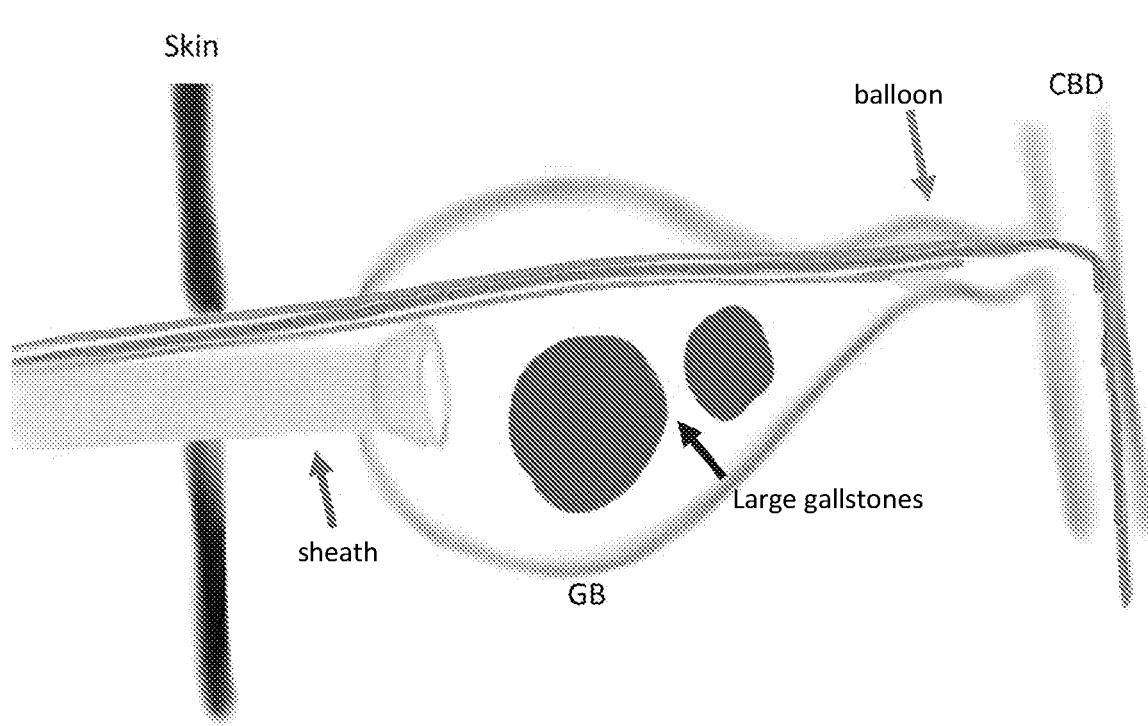
Figure 3G:
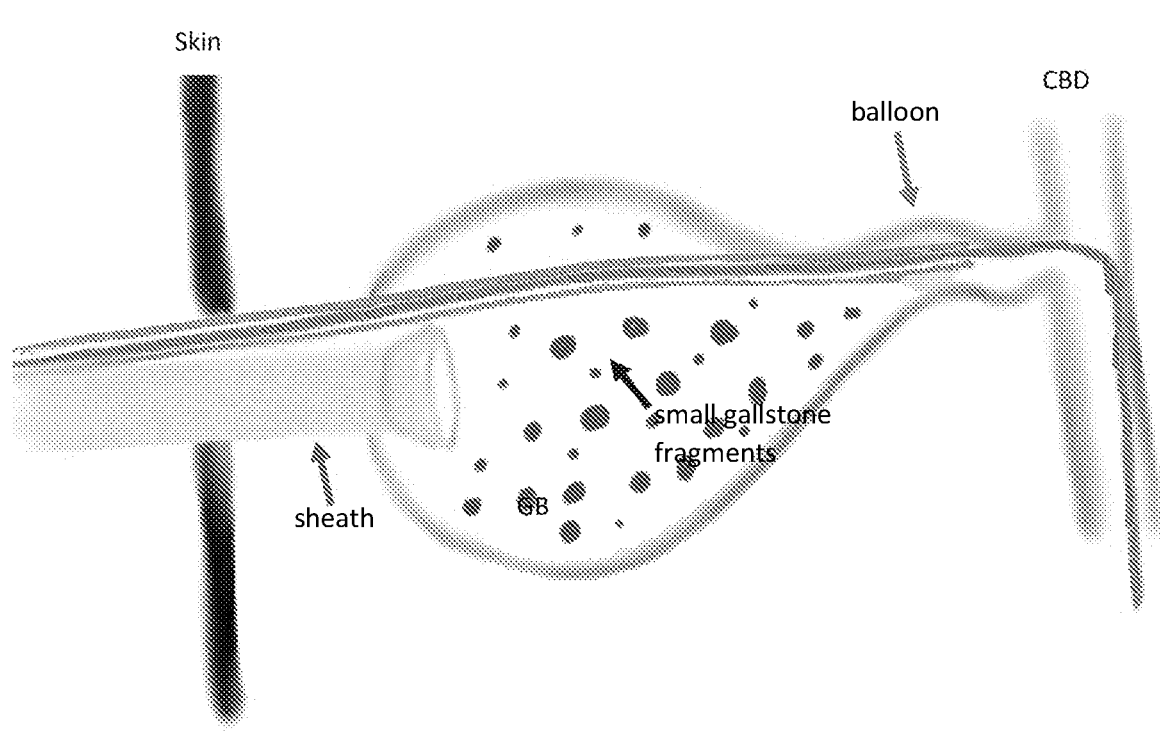

In some embodiments, solid deposits (e.g., stones) within an organ (e.g., gallbladder, kidney, etc.) are broken into smaller pieces using lithotripsy (FIGS. 3F and 3G). Lithotripsy entails shattering a concretion, such as a mineral deposit, (by light, chemical, or physical energy). Extracorporeal lithotripsy methods utilize energy generated outside the subject to break apart the deposits. Intracorporeal lithotripsy methods utilize energy generated within the subject or organ via a device delivered through the sheath or an endoscope. In some embodiments, extracorporeal or intracorporeal lithotripsy methods may be utilized in methods herein. Exemplary lithotripsy methods that may find use in embodiments herein, and are understood in the field include ultrasonic lithotripsy, holmium laser lithotripsy (YAG), thulium fiber laser lithotripsy, super pulse thulium fiber laser lithotripsy, pneumatic lithotripsy, electrohydraulic lithotripsy, etc.

In exemplary extracorporeal lithotripsy methods, the energy source emanates from outside the patient's body, such as but not limited to, a lithotripter (e.g., lithotripsy generator), and travels through the patient's body until reaching the concretion targeted for fragmentation in a process called extracorporeal shock wave lithotripsy (ESWL). Various lithotriptors and methods exist for generating high-intensity, focused shock waves for the fragmentation of stones inside the subject. A lithotriptor generating a spark gap discharge in water has been used to generate a shock wave within an ellipsoidal reflector, which couples and focuses the shock wave to fragment kidney stones inside the subject, using fluoroscopic or ultrasonic imaging to target the stone. Lithotriptors also exist that use a coil, in the form of a spherical segment, to produce magnetically induced self-converging shock waves that can be directed at a stone within the subject. Lithotriptor may also include piezoelectric elements to produce focused high-intensity shock waves. In some embodiments, the treatment of stones by extracorporeal lithotripsy apparatus requires a locating system, for correctly positioning the lithotripsy apparatus and the subject relative to each other so that the concretion, such as a kidney stone, is located in the focus of the shock waves. Ultrasound or fluoroscopic imaging may be used for this purpose. Alternatively, an endoscope-mounted camera, inserted through the sheath can be used for locating stones. In some embodiments, lithotripsy is performed without prior sub-organ localization of the stones. Using the lithotripsy apparatus, the focused shock waves are then passed into the subject, and act on the stone to disintegrate it into fragments.

Intracorporeal lithotripsy is a minimally invasive form of lithotripsy. Intracorporeal lithotripsy uses an endoscopic probe that is positioned within the organ in proximity to the concretion(s). The energy required for fragmentation is transferred through the probe to the concretion and the treatment process is visualized during fragmentation. The mode of energy transfer varies and differs depending on the physiological presentation of the renal stone. Particular examples of intracorporeal lithotripsy, all of which can be utilized in the described methods, are laser, ultrasonic, and ballistic (e.g., pneumatic) lithotripsy.

Figure 3H:
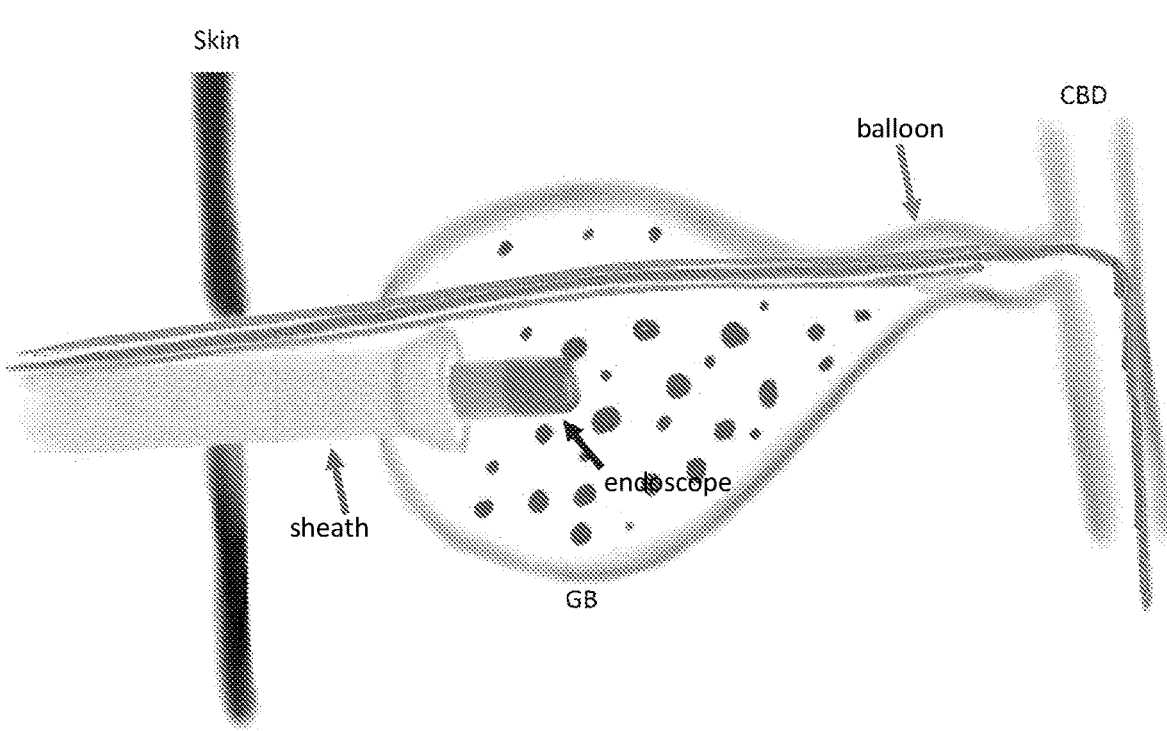

In some embodiments, an endoscope is advanced through the sheath to allow for various method steps to be performed (FIG. 3H). In some embodiments, the endoscope is placed with the distal end of the endoscope extending into the organ, beyond the distal end of the sheath. In some embodiments, the endoscope is placed with the distal end of the endoscope residing within the distal end of the sheath. In some embodiments, the position of the distal end of the endoscope relative to the organ and the distal end of the sheath can be altered/adjusted during the various steps of the methods herein. For example, the endoscope may be extended beyond the distal end of the sheath and into the organ to visualize the stones (e.g., number, size, characteristic, etc.). However, the endoscope may be retracted into the sheath for lithotripsy, flushing the organ, etc. Endoscope controls located at the proximal end of the endoscope (outside the patient) allow the positions and functions of the endoscope to be controlled by an operator.

Figure 3I:
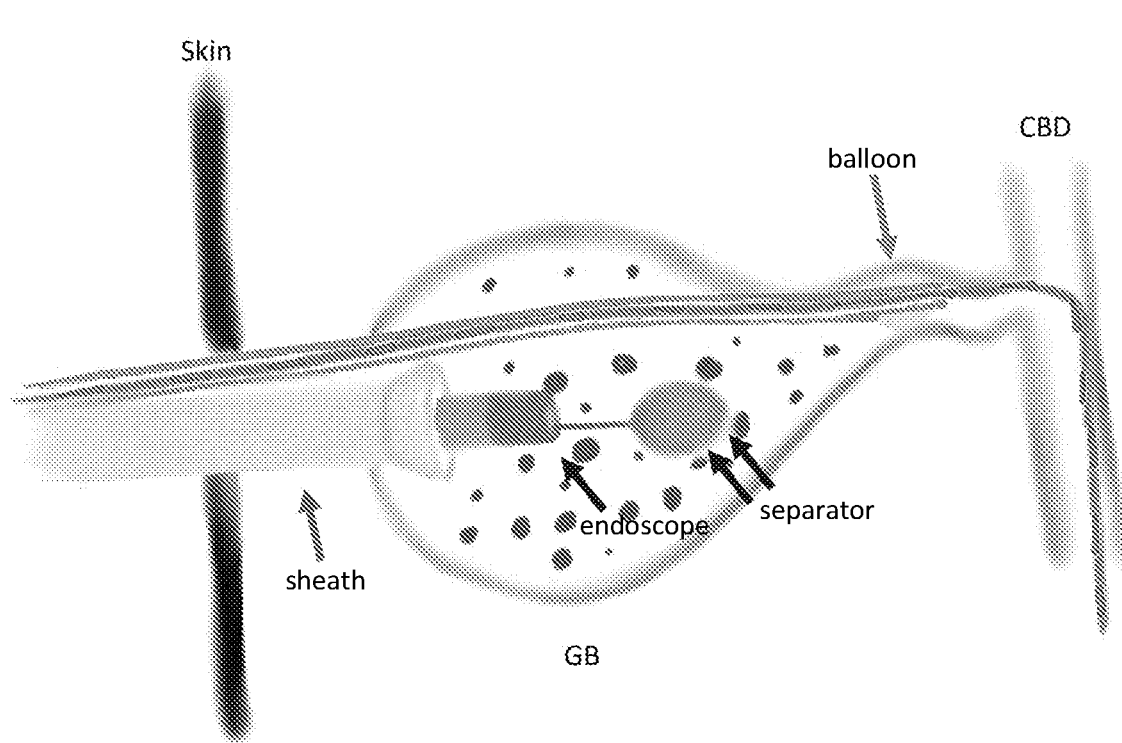
Figure 3J:
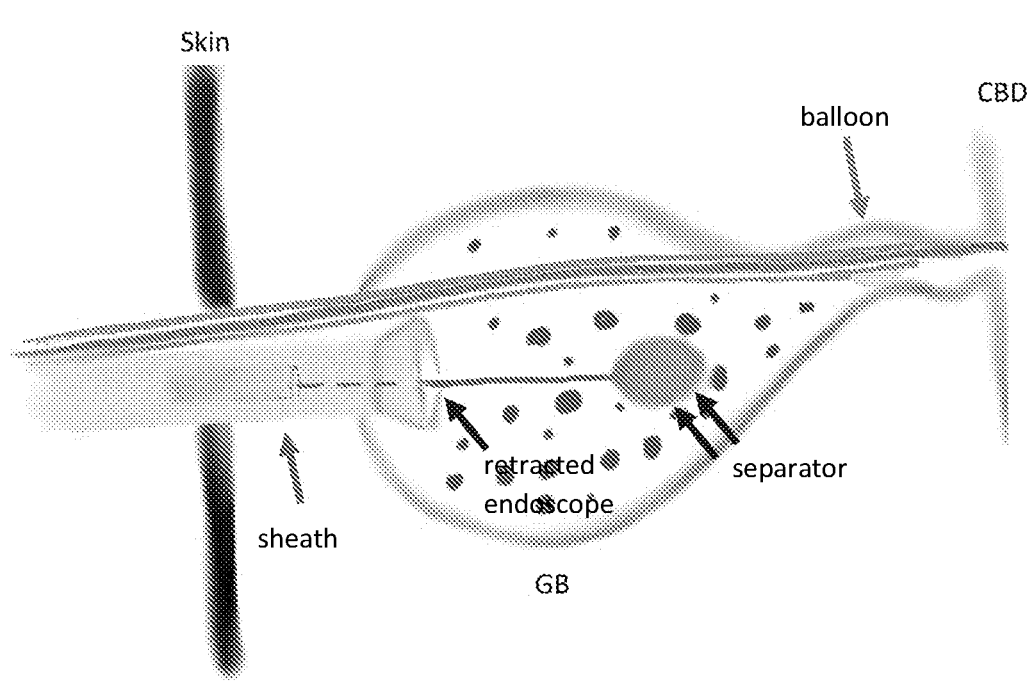
Figure 3K:
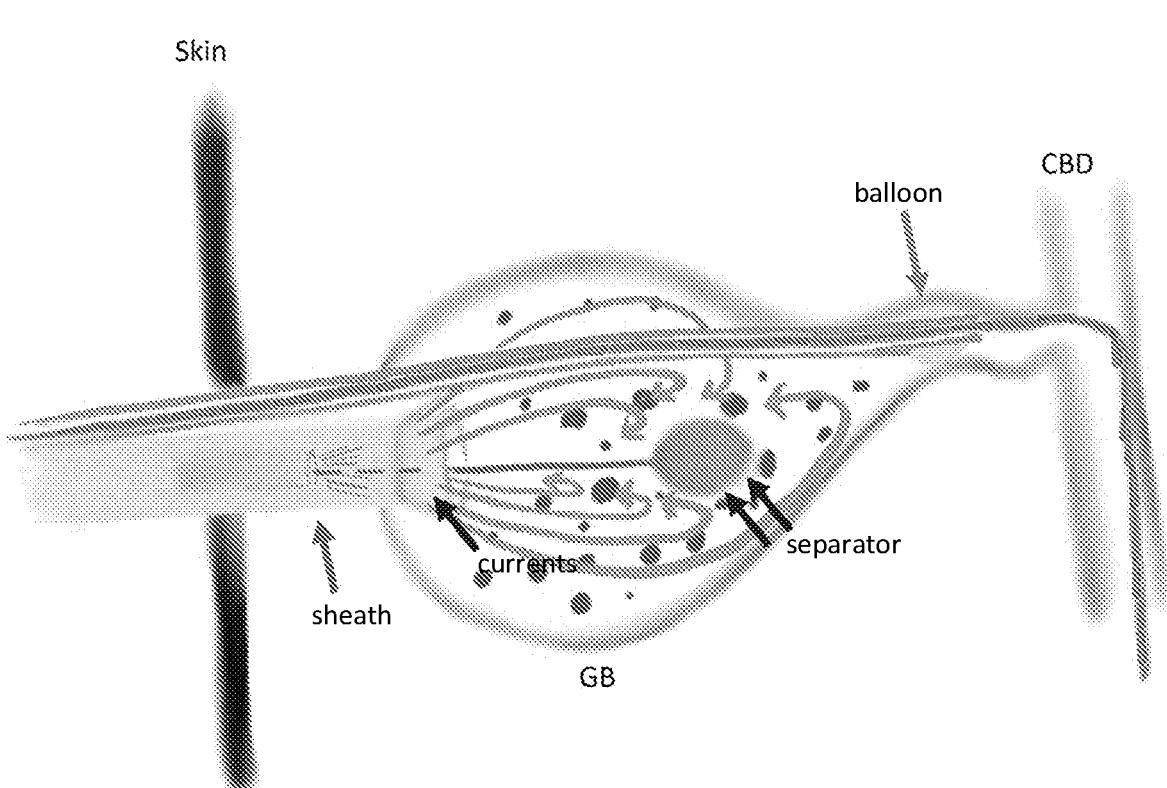
Figure 3L:
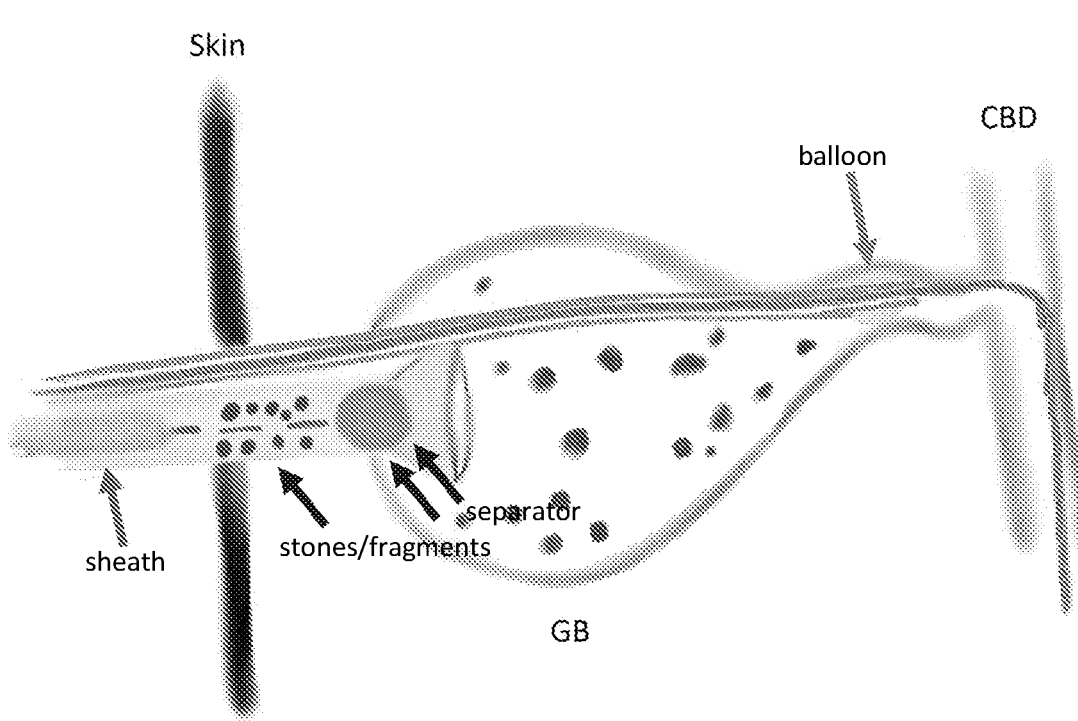

In some embodiments, an endoscope used in embodiments herein comprises one or more functionalities and components that are understood by those in the field. In some embodiments, an endoscope comprises a camera and light that facilitate visualization of the inside of the organ (kidney, gallbladder, etc.) and the deposits. In some embodiments, a channel is provided through the endoscope to allow an operator to control the light/camera and to visualize the inside of the organ (kidney, gallbladder, etc.) and the deposits. In some embodiments, the endoscope comprises one or more lumens/channels through which various devices or components of the systems herein can be advanced/withdrawn. For example, a lithotripsy device (e.g., laser) can be advanced through a lumen of the endoscope and into the organ. As another example, a separator element can be deployed from a channel of the endoscope and into the organ. The endoscope may also comprise a fluid outflow channel for delivering flush fluid to the organ. In some embodiments, the fluid outflow channel of the endoscope may terminate in a nozzle, sprayer, or other fluidic element that allows the flow of fluid to be appropriately directed within the organ. In some embodiments, fluid is delivered to the organ through the outflow. The endoscope may also comprise a fluid inflow channel for withdrawing flush fluid from the organ. In some embodiments, the combination of fluid outflow and fluid inflow form the channels of the endoscope creates currents within the organ that draw the stones/fragments into the distal end of the sheath (FIG. 3K). In some embodiments, the endoscope comprises both an inflow channel and an outflow channel. In other embodiments, the endoscope comprises only an inflow channel or an outflow channel. The endoscope may further comprise other additional components or functionalities to assist in the methods herein, consistent with the understanding in the field.

In some embodiments, a separator element is deployed into the organ. In some embodiments, a separator is deployed into the organ via the endoscope (FIG. 3I). In some embodiments, the separator is used to trap stones/fragments within the distal end of the sheath. In some embodiments, a separator is advanced through a working channel of the endoscope and deployed into the organ. In some embodiments, once stones/fragments are drawn into the end of the sheath by the currents generated by the flush fluid, the separator is withdrawn into the distal end of the sheath. In some embodiments, the endoscope is retracted into the sheath while the separator remains outside the sheath in the organ interior, thereby creating a space within the distal end of the sheath (FIG. 3J). In some embodiments, the separator is a balloon or umbrella element. In some embodiments, the separator is compliant and capable of adopting an expanded conformation that approximates the interior lumen of the sheath.

Figure 4A:
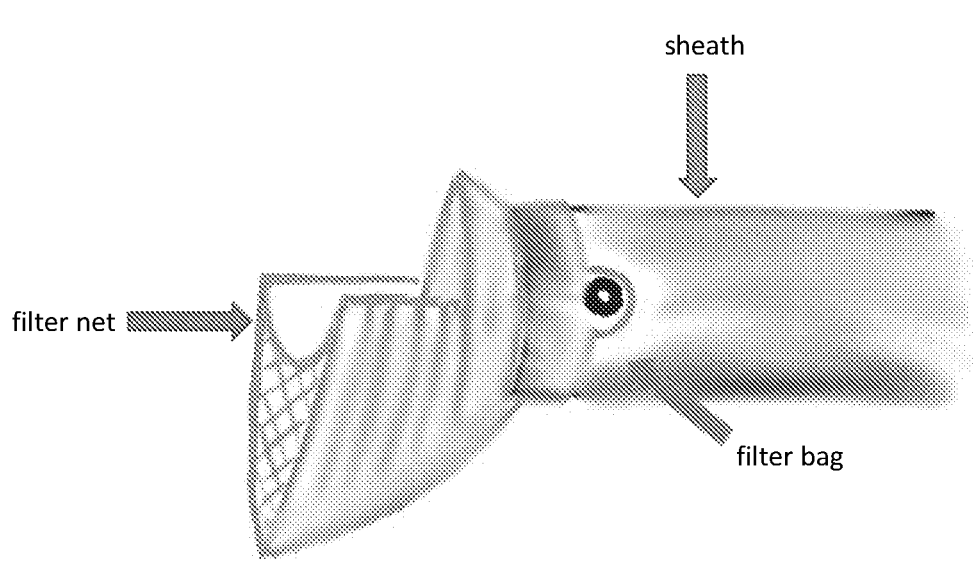
FIG. 4A-B. Proximal end of an exemplary sheath (A) Sheath comprising knobs for connection of a filter/bag, filter net that prevents stones/fragments from proceeding to the drain bag; and (B) Exemplary drain bag to collect bile/fluid flush with a reinforced spine that will allow the bag to rest beside the patient and not pull on the sheath; spigot-like opening to drain the fluid from the drain bag.
Figure 4B:
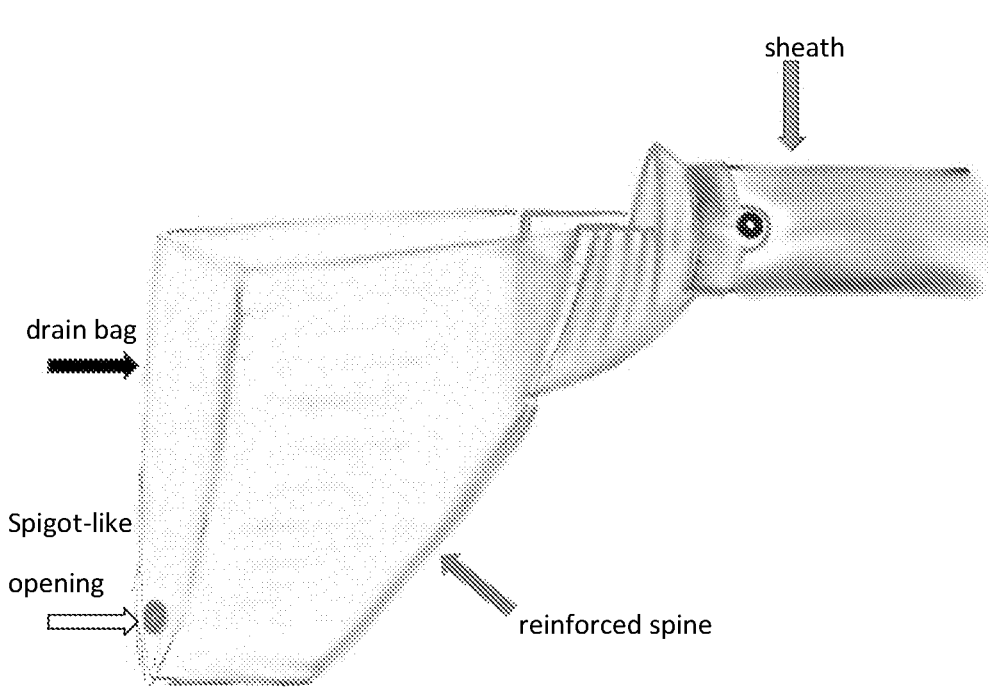

In some embodiments, stones are withdrawn through the sheath by retracting the separator through the sheath. In some embodiments, the proximal end may comprise a filter, bag, basket, or other elements for collecting the stones/fragments and the outflow fluid (FIGS. 4A and 4B). In some embodiments, the proximal end of the sheath comprises connectors (e.g., knobs, slots, etc. for connection of a filter/bag, filter net or other components for collection. In some embodiments, a filter, mesh material, netting, or other filtration component at the proximal end of the sheath collects stones/fragments as they exit the sheath. In some embodiments, the filter, mesh material, netting, or other filtration component allow the flush fluid to pass through. In some embodiments, the flush fluid is collected in a bag or other vessel. In some embodiments, the collection vessel can be emptied via a spigot or other component.

The invention claimed is:

1. A method for the percutaneous removal of solid deposits from an internal organ of a subject, the method comprising:

(a) accessing a percutaneous access tract into the internal organ;

(b) inserting a guidewire via the percutaneous access tract, into the internal organ, and into an exit channel for the internal organ;

(c) advancing an expandable occlusion element along the guidewire and positioning the expandable occlusion element within the exit channel;

(d) expanding the expandable occlusion element to obstruct outflow from the internal organ through the exit channel;

(e) inserting a sheath, into the internal organ via the percutaneous access tract;

(f) performing lithotripsy to degrade the stones into smaller fragments;

(g) advancing a separator through the sheath and into the internal organ;

(h) applying a high-pressure flush from the end of the sheath and creating currents within the internal organ that carry the stones and/or fragments thereof into the sheath; and (i) retracting the separator into the distal end of the sheath, thereby trapping the stones and/or fragments thereof within the sheath.

2. The method of claim 1, further comprising a step of:

(j) retracting the sheath through the percutaneous access tract, thereby removing the trapped stones and/or fragments thereof from the internal organ; or retracting the separator through the sheath, thereby removing the trapped stones and/or fragments thereof from the internal organ.

3. The method of claim 2, further comprising:

(k) collecting the stones or fragments thereof in a filter at the proximal end of the sheath.

4. The method of claim 3, further comprising:

(l) collecting the liquid is a collection vessel.

5. The method of claim 2, further comprising repeating steps (g)-(j) one or more times.

6. The method of claim 1, wherein: the internal organ is a gallbladder, and the exit channel is a cystic duct and/or common bile duct; or the internal organ is a kidney, and the exit channel is a ureter.

7. The method of claim 1, further comprising steps of advancing an expandable deformation element through the sheath; positioning it within the distal end of the sheath; expanding the expandable deformation element to deform the distal end of the sheath into a funnel shape; contracting the expandable deformation element into a low-profile conformation and retracting the expandable deformation element through the sheath, wherein the distal end of maintains the funnel shape upon contracting and retracting the expandable deformation element.

8. The method of claim 7, wherein the expandable deformation element is a balloon or umbrella element.

9. The method of claim 1, further comprising advancing an endoscope through the sheath and into the internal organ.

10. The method of claim 9, further comprising visualizing the internal organ and/or the stones or smaller fragments thereof with a camera near the distal end of the endoscope.

11. The method of claim 9, wherein step (g) comprises advancing the separator through the endoscope and into the internal organ.

12. The method of claim 1, wherein the separator is a balloon or umbrella element capable being advanced and retracted through the sheath and also capable of occluding the interior of the sheath to (i) prevent escape of the stones or fragments thereof from the sheath and (ii) to remove the stones or fragments thereof from the sheath as the separator is retracted through the sheath.

13. The method of claim 1, wherein creating a percutaneous access tract comprises creating incisions in the skin of the subject and the exterior surface of the internal organ.

14. The method of claim 1, wherein the expandable occlusion element is a balloon or umbrella element capable of adopting a collapsed conformation for being advanced along the guidewire and an expanded conformation for obstructing the exit channel of the internal organ.

15. The method of claim 1, wherein the lithotripsy comprises extracorporeal shockwave lithotripsy, laser lithotripsy, or electrohydraulic lithotripsy.

16. A system for the percutaneous removal of solid deposits from an internal organ within a subject, the system comprising:

(a) a guidewire;

(b) an expandable occlusion element capable of (1) being advanced along the guidewire, (2) being positioned at a desired position along the guidewire, and (3) adopting an expanded conformation at the desired positioned along the guidewire;

(c) a sheath comprising: (1) a proximal end configured to be positioned outside of the subject, (2) a distal end configured to be positioned within the internal organ, and (3) an inner lumen extending from there proximal end to the distal end;

(d) a lithotripsy generator;

(e) a separator element capable of (1) being advanced through the inner lumen of the sheath into the internal organ, (2) occluding the lumen of the sheath upon being retracted into the distal end of the sheath, and (3) withdrawing the contents of the inner lumen of the sheath from the subject upon being retracted through the inner lumen of the sheath.

* * * * *